United States Patent [19]
Ecker et al.

[11] Patent Number: 5,955,652
[45] Date of Patent: Sep. 21, 1999

[54] PLANT GENES FOR SENSITIVITY TO ETHYLENE AND PATHOGENS

[75] Inventors: Joseph Ecker, Erial, N.J.; Jose Alonso, Philadelphia, Pa.

[73] Assignee: The Trustees of the University of Pennsylvania, Philadelphia, Pa.

[21] Appl. No.: 08/819,288

[22] Filed: Mar. 18, 1997

Related U.S. Application Data

[63] Continuation-in-part of application No. 08/261,822, Jun. 17, 1994, Pat. No. 5,650,553, and application No. 08/171,207, Dec. 21, 1993, Pat. No. 5,674,701, which is a continuation of application No. 07/899,262, Jun. 16, 1992, abandoned, said application No. 08/261,822, is a continuation-in-part of application No. 08/033,311, Jan. 12, 1993, Pat. No. 5,444,166, which is a continuation-in-part of application No. 07/928,464, Aug. 10, 1992, Pat. No. 5,367,065.

[51] Int. Cl.$^6$ .............................. A01H 5/00; C12N 5/14; C12N 15/29; C12N 15/82
[52] U.S. Cl. ....................... 800/298; 435/320.1; 435/419; 435/468; 536/23.6; 800/278; 800/283
[58] Field of Search ......................... 536/23.6; 435/172.3, 435/320.1, 419; 800/205

[56] References Cited

U.S. PATENT DOCUMENTS

| | | | |
|---|---|---|---|
| 5,073,676 | 12/1991 | Bridges et al. | 800/205 |
| 5,650,553 | 7/1997 | Ecker et al. | 800/205 |
| 5,670,367 | 9/1997 | Dorner et al. | 435/320.1 |

FOREIGN PATENT DOCUMENTS

| | | |
|---|---|---|
| WO 94/03047 | 2/1994 | WIPO. |
| WO 95/35318 | 12/1995 | WIPO. |

OTHER PUBLICATIONS

Chang, C. et al., "Arabidopsis Ethylene–Response Gene ETR1: Similarity of Product to Two–Component Regulators", *Science*, 1993, 262, 539–543.

Desprez, T. et al., "A. Thaliana transcribed sequence; clone VBVPD10", *Embl. Sequence Database*, Mar. 29, 1995, Rel. 43, Accession No. F13816, 1 page.

Ecker, J.R. et al., "The Ethylene Sensing Apparatus in Arabidopsis", *Suppl. Plant Physiology*, 1994, 105(1), 1 page, Abstract No. 40002.

Kieber, J.J. et al., "Ethylene gas: it's not just for ripening any more!", *TIG*, 1993, 9(10), 356–362.

Lehman, A.L., "Molecular and Genetic Characterization of the Hookless Mutants in Arabidopsis Thaliana (Differentiation, Ethylene, Auxins)", *Dissertation Abstracts International*, 1995, 57(1B), p. 128, (Order No. AA19615075, 98 pages).

Newman, T. et al., "13777 Arabidopsis thaliana cDNA clone 168H7T7", *Embl. Sequence Database*, Jun. 4, 1995, Rel. 44, Accession No. R65273, 1 page.

Newman, T. et al., "15568 Arabidopsis thaliana cDNA clone 181J20T7", *Embl. Sequence Database*, Jul. 27, 1995, Rel. 44, Accession NO. H37439, 1 page.

Roman, G.W., "Genetic Analysis of Ethylene Signal Transduction and the Positional Cloning of the EIN2 Locus of Arabidopsis Thaliana", *Dissertation Abstracts International*, 1995, 56(5B), p. 2443, (Order No. AA19532265, 124 pages.

Abel et al., "Transient transformation of Arabidopsis leaf protoplasts: a versatile experimental system to study gene expression", *Plant J.*, 1994, 5, 421–427.

Abeles et al., *Ethylene In Plant Biology*, Second Edition, 1992.

Agrios, "Genetics of Plant Disease", *Plant Pathology*, Academic Press, San Diego, 1988, Ch. 6, 126.

Bell et al., *Methods in Plant Molecular Biology: A Laboratory Manual*, 1993, Maliga, Klessig, and Cashmore (eds.), Cold Spring Harbor Laboratory.

Bent et al., "Disease Development in Ethylene–Insensitive *Arabidopsis thaliana* Infected with Virulent and Avirulent Pseudomonas and Xanthomonas Pathogens", *Molecular Plant–Microbe Interactions*, 1992, 5, 372–378.

Bleecker et al., "Insensitivity to Ethylene Conferred by a Dominant Mutation in *Arabidopsis thaliana*", *Science*, 1988, 241, 1086–1089.

Blinder et al., "Constitutive Mutants in the Yeast Pheromone Response: Ordered Function of the Gene Products", *Cell*, 1989, 56, 479–486.

Boller, "The Plant Hormone Ethylene", A. K. Mattoo and J. C. Suttle (eds.), CRC Press, Inc., Boca Raton, 1991, 293–314.

Chang et al., "Restriction fragment length polymorphism linkage map for *Arabiopsis thaliana*", *Proc. Natl. Acad. Sci. USA*, 1988, 85, 6857.

Clark et al., "On the Identification of the Rosy Locus DNA in Drosophila Melanogaster: Intragenic Recombination Mapping of Mutations Associated with Insertions and Deletions", *Genetics*, 1986, 112, 755.

Debener et al., "Identification and Molecular Mapping of a Single *Arabidopsis thaliana* Locus Determining Resistance to a Phytopathogenic *Pseudomonas syringae* Isolate", *Plant J.*, 1991, 1, 289.

Dong et al., "Induction of Arabidopsis Defense Genes by Virulent and Avirulent *Pseudomonas synringae* Strains and by a Cloned Avirulence Gene", *Plant Cell*, 1991, 3, 61.

Feinberg et al., "A Technique for Radiolabeling DNA Restrictionn Endonuclease Fragments to High Specific Activity", *Anal. Biochem.*, 1984, 177, 266–267.

Feldmann et al., "Agrobacterium–mediated transformation of germinating seeds of *Arabidopsis thaliana:* A non–tissue culture approach", *Mol. Gen. Genet.*, 1987, 208, 1–9.

Gray et al., "Molecular biology of fruit ripening and its manipulation with antisense genes", *Plant Mol Biol.*, 1992, 19, 69–87.

(List continued on next page.)

Primary Examiner—Douglas W. Robinson
Assistant Examiner—Amy J. Nelson
Attorney, Agent, or Firm—Woodcock Washburn Kurtz Mackiewicz & Norris LLP

[57] ABSTRACT

The present invention is directed to nucleic acid sequences for ethylene insensitive, EIN loci and corresponding amino acid sequences.

5 Claims, 2 Drawing Sheets

OTHER PUBLICATIONS

Grill et al., "Construction and characterization of a yeast artificial chromosome library of Arabidopsis which is suitable for chromosome walking", *Mol. Gen. Genet.,* 1991, 226, 484–490.

Guzman et al., "Exploiting the Triple Response of Arabidopsis to Identify Ethylene–Related Mutants", *Plant Cell,* 1990, 2, 513–523.

Harpman et al., "The Effect of Ethylene on the Growth and Development of Wild–type and Mutant *Arabidopsis Tahliana* Heynh", *Annals of Botany,* 1991, 68, 55.

Jefferson et al., "GUS fusions: β–Glucuronidase as a sensitive and versatile gene fusion marker in higher plants", *EMBO J.* 1987, 6, 3901–3907.

Kende, "Enzymes of Ethylene Biosynthesis", *Plant Physiol.,* 1989, 91, 1–4.

Kieber et al., "CTR1, a Negative Regulator of the Ethylene Response Pathway in Arabidopsis, Encodes a member of the Raf Family of Protein Kinases", *Cell,* 1993, 72, 427–441.

Klee et al., "Molecular Genetic Approaches to Plant Hormone Biology", *Annual Review of Plant Physiology,* 1991, 42, 529–551.

Koornneef et al., *Methods in Arabidopsis Research,* C. Koncz, N–H Chua, and J. Schell (eds.), 1992, World Scientific Publishing Co., Singapore.

McGarvey et al., "Ripening–Related Gene from Avocado Fruit", *Plant Physiol.,* 1992, 98, 554.

Matallana et al., "Genetic and Pysical Linkage of the Arabidopsis Genome: Methods for Anchoring Yeast Artificial Chromosomes", *Methods in Arabidopsis Research,* C. Koncz, N–H Chua, and J. Schell (eds.), 1992, Ch. 6, World Scientific Publishing Co., Singapore.

Mussel, "Tolerance to Disease", p. 40, in *Plant Disease: An Advanced Treatise,* vol. 5, Horsfall, J.G. and Cowling, E.B., eds., 1980, Academic Press, New York.

Nakajima et al., "Molecular Cloning and Sequence of a Complementary DNA Encoding 1–Aminocyclopropane–1–carboxylate Synthase Induced by Tissue Wounding", *Plant Cell Physiol.,* 1990, 29, 989.

Nakajima et al., "Molecular Cloning and Sequence of a Complementary DNA Encoding 1–Aminocyclopropane–1–carboxylate Synthase Induced by Tissue Wounding", *Plant Cell Physiol.,* 1990, 31(7), 1021–1029.

Nam et al., "Restriction Fragment Length Polymorphism Linkage Map of *Arabidopsis thaliana*", *Plant Cell,* 1990, 1, 699.

Neljubow, *Pflanzen Beih. Bot. Zentralb.,* 1901, 10, 128.

Reardon et al., "Molecular Analysis of Diepoxybutane–Induced Mutations at the Rosy Locus of Drosophila melanogaster", *Genetics,* 1987, 115, 323.

Restrepo et al., "Nuclear Transport of Plant Potyviral Proteins", *Plant Cell* 1990, 2, 987–998.

Rubenstein, "Characteristics of Hook Formation by Bean Seedlings", *Plant Physiology,* 1972, 49, 640–643.

Sambrook et al., *Molecular Cloning: A Laboratory Manual,* 2nd ed., 1989, Cold Spring Harbor Laboratory Press, Cold Spring Harbor, NY.

Sato et al., "Cloning the mRNA encoding 1–aminocyclopropan–1–carboxylate syntase the key enzyme for ethylene biosynthesis in plants", *Proc. Natl. Acad. Sci.,* 1989, 86, 6621–6625.

Spanu et al., "Analysis and Cloning of the Ethylene–forming enzyme from tomato by functional expression of its mRNA in Xenopus Laevis oocytes", *EMBO J.,* 1991, 10, 2007–2013.

Tercero, "Localized Mutagenesis and Evidence for Post–transcriptional Regulation of MAK3", *JBC,* 1992, 267, 20270.

Theologis, "One Rotten Apple Spoils the Whole Bushel: The Role of Ethylene in Fruit Ripening", *Cell,* 1992, 70, 181.

Van Der Straeten et al., "Cloning and sequence of two different cDNAs encoding 1–aminocyclopropane–1–carboxylate synthase in tomato", *Proc. Natl. Acac. Sci.,* 1990, 87, 4859–4863.

Velvekins et al., "Agrobacterium tumefaciens–mediated transformation of Arabidopsis taliana root explants by using kanamycin selection", *PNAS,* 1988, 85, 5536–5540.

Whalen et al., "Identification of Pseudomonas synringae Pathogens of Arabidopsis and a Bacterial Locus Determining Avirulence on Both Arabidopsis and Soybean", *Plant Cell,* 1991, 3, 49–59.

Yang et al., "Ethylene Biosynthesis and its Regulation in Higher Plants", *Ann. Rev. Plant Physiol.,* 1984, 35, 155.

Yu et al., "Regulation of Auxin–induced Ethylene Production in Mung Bean Hypocotyls", *Plant Physiol.,* 1979, 63, 589–590.

Koncz et al., "High–frequency T–DNA–mediated Gene Tagging in Plants", *Proc. Natl. Acad. Sci. USA,* 1989, 86, 8467–8471.

Hanks et al., "The Protein Kinase Family: Conserved Features and Deduced Phylogeny of the Catalytic Domains", *Science,* 1988, 241, 42–52.

Scott, "Plant Hormone Response Mutants", *Physiol. Plantarum,* 1990, 78, 147–152.

Bechtold et al., "In planta Agrobacterium–mediated transfer by infiltration of adult *Arabidopsis thaliana* plants", *Comptes rendus de Academic des Sciences,* 1993, 316, 1194–1199.

Doyle et al., "A Rapid DNA Isolation Procedure for Small Quantities of Fresh Leaf Tissue", *Phytochem. Buee,* 1987, 19(1), 11–15.

Schardl et al., "Design and construction of a versatile system for the expression of foreign genes in plants", *Gene,* 1987, 61, 1–11.

CONSTUCTION OF pKYLX7:cEIN2

PLANT GENES FOR SENSITIVITY TO ETHYLENE AND PATHOGENS

REFERENCE TO RELATED APPLICATIONS

This application is a continuation-in-part of U.S. application Ser. No. 08/261,822, filed Jun. 17, 1994, now U.S. Pat. No. 5,650,553, which is a continuation-in-part of U.S. application Ser. No. 08/003,311, filed Jan. 12, 1993, now U.S. Pat. No. 5,444,166, which is a continuation-in-part of U.S. application Ser. No. 07/928,464, filed Aug. 10, 1992, now U.S. Pat. No. 5,367,065; this application is also a continuation-in-part of U.S. application Ser. No. 08/171,207, filed Dec. 21, 1993, now U.S. Pat. No. 5,674,701, which is a continuation of U.S. application Ser. No. 07/899,262, filed Jun. 16, 1992, now abandoned; the disclosures of each of which are hereby incorporated in their entirety.

REFERENCE TO GOVERNMENT GRANTS

This work was supported in part by research grants from the National Institutes of Health GM-26379 and National Science Foundation grant IBN-92-05342. The United States Government may have certain rights in this invention.

BACKGROUND OF THE INVENTION

Ethylene, a gaseous plant hormone, is involved in the regulation of a number of plant processes ranging from growth and development to fruit ripening. As in animal systems, response of plants to disease not only involves static processes, but also involves inducible defense mechanisms. One of the earliest detectable event to occur during plant-pathogen interaction is a rapid increase in ethylene biosynthesis. Ethylene biosynthesis, in response to pathogen invasion, correlates with increased defense mechanisms, chlorosis, senescence and abscission. The molecular mechanisms underlying operation of ethylene action, however, are unknown. Nonetheless, ethylene produced in response to biological stress is known to regulate the rate of transcription of specific plant genes. A variety of biological stresses can induce ethylene production in plants including wounding, bacterial, viral or fungal infection as can treatment with elicitors, such as glycopeptide elicitor preparations (prepared by chemical extraction from fungal pathogen cells). Researchers have found, for example, that treatment of plants with ethylene generally increases the level of many pathogen-inducible "defense proteins", including β-1,3-glucanase, chitinase, L-phenylalanine ammonia lyase, and hydroxyproline-rich glycoproteins. The genes for these proteins can be transcriptionally activated by ethylene and their expression can be blocked by inhibitors of ethylene biosynthesis. Researchers have also characterized a normal plant response to the production or administration of ethylene, as a so-called "triple response". The triple response involves inhibition of root and stem elongation, radial swelling of the stem and absence of normal geotropic response (diageotropism).

Ethylene is one of five well-established plant hormones. It mediates a diverse array of plant responses including fruit ripening, leaf abscission and flower senescence.

The pathway for ethylene biosynthesis has been established. Methionine is converted to ethylene with S-adenylmethionine (SAM) and 1-aminocyclopropane-1-carboxylic acid (ACC) as intermediates. The production of ACC from SAM is catalyzed by the enzyme ACC synthase. Physiological analysis has suggested that this is the key regulatory step in the pathway, see Kende, *Plant Physiol.* 1989, 91, 1–4. This enzyme has been cloned from several sources, see Sato et al., *PNAS, (USA)* 1989, 86, 6621; Van Der Straeten et al., *PNAS, (USA)* 1990, 87, 4859–4863; Nakajima et al., *Plant Cell Physiol.* 1990, 29, 989. The conversion of ACC to ethylene is catalyzed by ethylene forming enzyme (EFE), which has been recently cloned (Spanu et al., *EMBO J* 1991, 10, 2007. Aminoethoxy-vinylglycine (AVG) and α-aminoisobutyric acid (AIB) have been shown to inhibit ACC synthase and EFE respectively. Ethylene binding is inhibited non-competitively by silver, and competitively by several compounds, the most effective of which is trans-cyclooctane. ACC synthase is encoded by a highly divergent gene family in tomato and Arabidopsis (Theologis, A., *Cell* 70:181 (1992)). ACC oxidase, which converts ACC to ethylene, is expressed constitutively in most tissues (Yang et al., *Ann. Rev. Plant Physiol.* 1984, 35, 155), but is induced during fruit ripening (Gray et al. *Cell* 1993 72, 427). It has been shown to be a dioxygenase belonging to the $Fe^{2+}$/ascorbate oxidase superfamily (McGarvey et al., *Plant Physiol.* 1992, 98, 554).

Etiolated dicotyledonous seedlings are normally highly elongated and display an apical arch-shaped structure at the terminal part of the shoot axis; the apical hook. The effect of ethylene on dark grown seedlings, the triple response, was first described in peas by Neljubow in 1901, Neljubow, D., *Pflanzen Beih. Bot. Zentralb.*, 1901, 10, 128. In Arabidopsis, a typical triple response consists of a shortening and radial swelling of the hypocotyl, an inhibition of root elongation and an exaggeration of the curvature of the apical. Etiolated morphology is dramatically altered by stress conditions which induce ethylene production the ethylene-induced "triple response" may provide the seedling with additional strength required for penetration of compact soils, see Harpham et al., *Annals of Bot.*, 1991, 68, 55. Ethylene may also be important for other stress responses. ACC synthase gene expression and ethylene production is induced by many types of biological and physical stress, such as wounding and pathogen infection, see Boller, T., in *The Plant Hormone Ethylene*, A. K. Mattoo and J. C. Suttle eds., 293–314, 1991, CRC Press, Inc. Boca Raton and Yu, Y. et al., *Plant Phys.*, 1979, 63,589, Abeles et al. 1992 Second Edition San Diego, Calif. Academic Press; and Gray et al. *Plant Mol Biol.* 1992 19, 69.

A number of researchers have identified the interaction between *Arabidopsis thaliana* and *Pseudomonas syringae* bacteria; Whalen et al., "Identification of *Pseudomonas syringae* Pathogens of Arabidopsis and a Bacterial Locus Determining Avirulence on Both Arabidopsis and Soybean", *The Plant Cell* 1991, 3, 49, Dong et al., "Induction of Arabidopsis Defense Genes by Virulent and Avirulent *Pseudomonas syringae* Strains and by a Cloned Avirulence Gene", *The Plant Cell* 1991, 3, 61, and Debener et al., "Identification and Molecular Mapping of a Single *Arabidopsis thaliana* Locus Determining Resistance to a Phytopathogenic *Pseudomonas syringae* Isolate", *The Plant Journal* 1991, 1, 289. *P. syringae* pv. *tomato* (Pst) strains are pathogenic on Arabidopsis. A single bacterial gene, avrRpt2, was isolated that controls pathogen avirulence on specific Arabidopsis host genotype Col-0.

Bent, A. F., et al., "Disease Development in Ethylene-Insensitive *Arabidopsis thaliana* Infected with Virulent and Avirulent Pseudomonas and Xanthomonas Pathogens", *Molecular Plant-Microbe Interactions* 1992, 5, 372; Agrios, G. N., *Plant Pathology* 1988, 126, Academic Press, San Diego; and Mussel, H., "Tolerance to Disease", page 40, in *Plant Disease: An Advanced Treatise, Volume* 5, Horsfall, J. G. and Cowling, E. B., eds., 1980, Academic Press, New York, establish the art recognized definitions of tolerance, susceptibility, and resistance. Tolerance is defined for purposes of the present invention as growth of a pathogen in a plant where the plant does not sustain damage. Resistance is defined as the inability of a pathogen to grow in a plant and no damage to the plant results. Susceptibility is indicated by pathogen growth with plant damage.

Regardless of the molecular mechanisms involved, the normal ethylene response of a plant to pathogen invasion has been thought to have a cause and effect relationship in the ability of a plant to fight off plant pathogens. Plants insensitive in any fashion to ethylene were believed to be incapable of eliciting a proper defense response to pathogen invasion, and thus unable to initiate proper defense mechanisms. As such, ethylene insensitive plants were thought to be less disease tolerant.

The induction of disease responses in plants requires recognition of pathogens or pathogen-induced symptoms. In a large number of plant-pathogen interactions, successful resistance is observed when the plant has a resistance gene with functional specificity for pathogens that carry a particular avirulence gene. If the plant and pathogen carry resistance and avirulence genes with matched specificity, disease spread is curtailed and a hypersensitive response involving localized cell death and physical isolation of the pathogen typically occurs. In the absence of matched resistance and avirulence genes, colonization and tissue damage proceed past the site of initial infection and disease is observed.

A better understanding of plant pathogen tolerance is needed. Also needed is the development of methods for improving the tolerance of plants to pathogens, as well as the development of easy and efficient methods for identifying pathogen tolerant plants.

Genetic and molecular characterization of several gene loci and protein products is set forth in the present invention. The results will reveal interactions among modulatory components of the ethylene action pathway and provide insight into how plant hormones function. Thus, the quantity, quality and longevity of food, such as fruits and vegetables, and other plant products such as flowers, will be improved thereby providing more products for market in both developed and underdeveloped countries.

SUMMARY OF THE INVENTION

The present invention is directed to nucleic acid sequences for ethylene insensitive, EIN loci and corresponding amino acid sequences. Several ein wild type sequences, mutations, amino acid sequences, and protein products are included within the scope of the present invention. The nucleic acid sequences from *Arabidopsis thaliana* Columbia-0 strain set forth in SEQ ID NOS 1 and 2 for ein2 genomic DNA and cDNA, respectively, as well as the EIN2 amino acid sequence set forth in SEQ ID NO: 3 are particular embodiments of the present invention.

These and other aspects of the invention will become more apparent from the following detailed description.

BRIEF DESCRIPTION OF THE FIGURES

FIG. 2A displays Col-O wild-type plants, FIG. 2B displays transgenic pKYLX7:cEIN2-containing Col-O plants.

DETAILED DESCRIPTION OF THE INVENTION

Figure 1:
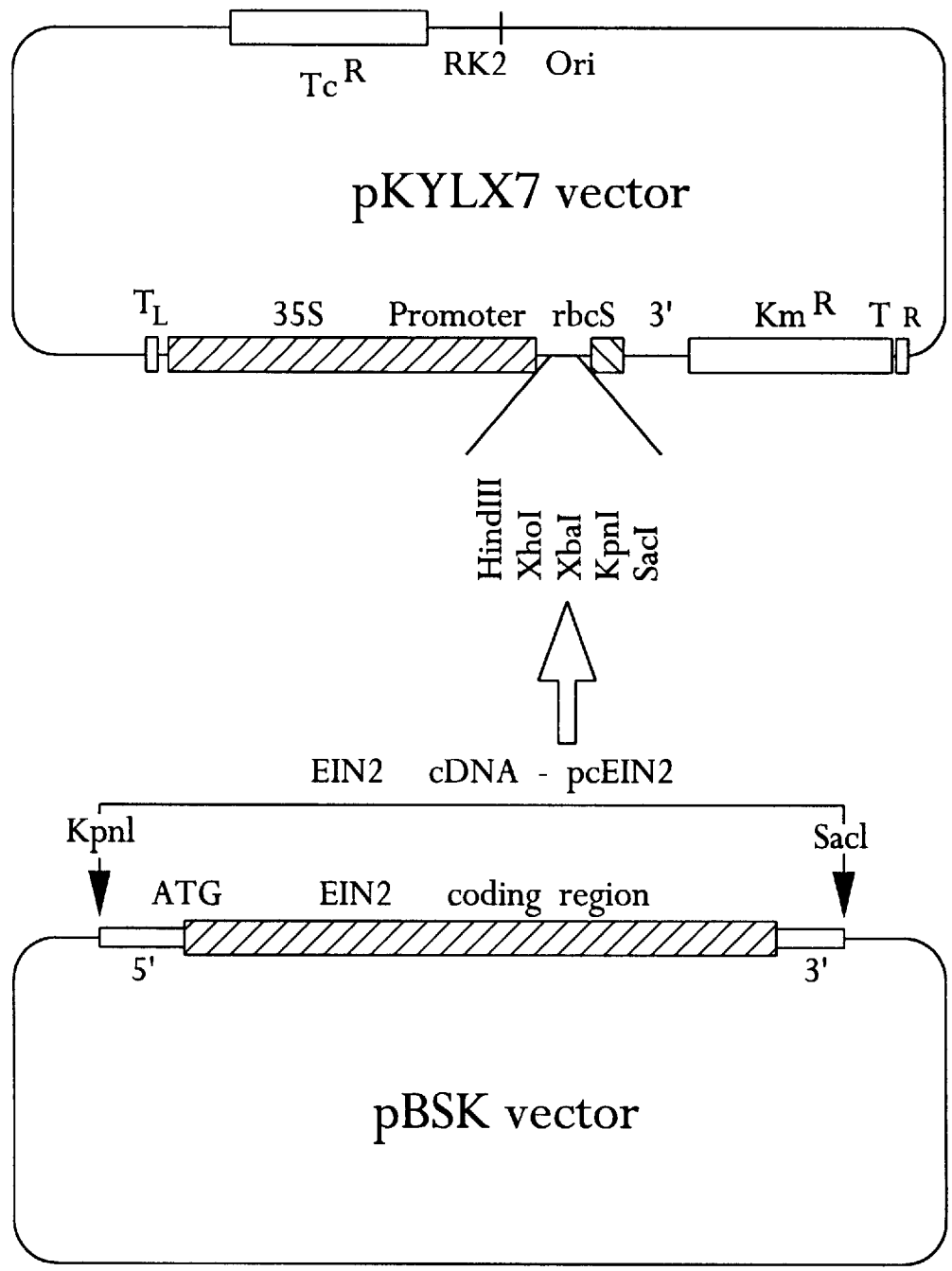
FIG. 1 sets forth the construction of pKYLX7:cEIN2 vector from pBSK:cEIN2 vector.

The present invention is directed to nucleic acid and amino acid sequences which lend valuable characteristics to plants.

The present invention is directed to nucleic acid sequences of the EIN2 locus of *Arabidopsis thaliana* Columbia-O strain. Wild type and mutant sequences of EIN2 are within the scope of the present invention. Amino acid and protein sequences corresponding to the nucleic acid sequences are included in the present invention. EIN2 mutations provide for ethylene insensitivity and pathogen tolerance in plants.

SEQ ID NO: 2, that provides for an isolated cDNA representing the nucleic acid sequence coding for EIN2, and SEQ ID NO: 1 that provides for an isolated genomic EIN2 sequence, are embodiments of the present invention. The purified amino acid sequence of SEQ ID NO: 3 represents the EIN2 amino acid sequence or protein product encoded by the cDNA identified above. A cDNA sequence represented by bases 584–4468 of SEQ ID NO: 2 encodes an amino acid sequence set forth in SEQ ID NO: 3, represented therein as amino acids 1–1295. EIN2 mutations identified herein by nucleotide position are measured in accordance with the beginning of the cDNA.

In accordance with the present invention, nucleic acid sequences include and are not limited to DNA, including and not limited to cDNA and genomic DNA; RNA, including and not limited to mRNA and tRNA; and suitable nucleic acid sequences such as those set forth in SEQ ID NOS set forth herein, and alterations in the nucleic acid sequences including alterations, deletions, mutations and homologs. In addition, mismatches within the sequences identified above, which achieve the methods of the invention, are also considered within the scope of the disclosure. The sequences may also be unmodified or modified. Any change in the sequences that permits substantially the same sequence to be useful in substantially the same way is within the scope of the present invention. In addition, the isolated, or purified, sequences of the present invention may be natural, recombinant, synthetic, or a combination thereof. Activity associated with the sequences of the present invention include, inter alia, all or part of a sequence of the present invention, or a sequence substantially similar thereto.

Also amino acid, peptide and protein sequences within the scope of the present invention include, and are not limited to, the sequences set forth herein and alterations in the amino acid sequences including alterations, deletions, mutations and homologs.

In accordance with the invention, the nucleic acid sequences employed in the invention may be exogenous/heterologous sequences. Exogenous and heterologous, as used herein, denote a nucleic acid sequence which is not obtained from and would not normally form a part of the genetic make-up of the plant or the cell to be transformed, in its untransformed state. Plants comprising exogenous nucleic acid sequences of EIN2 and ein2 mutations, such as and not limited to the nucleic acid sequences of SEQ ID NOS set forth herein are within the scope of the invention.

Transfected and/or transformed plant cells comprising nucleic acid sequences of EIN2 and ein2 mutations, such as and not limited to the nucleic acid sequences of SEQ ID NOS set forth herein, are within the scope of the invention. Transfected cells of the invention may be prepared by employing standard transfection techniques and procedures as set forth in Sambrook et al., *Molecular Cloning: A*

*Laboratory Manual*, 2nd ed., 1989, Cold Spring Harbor Laboratory Press, Cold Spring Harbor, N.Y., hereby incorporated by reference in its entirety.

In accordance with the present invention, mutant plants which may be created with the sequences of the claimed invention include higher and lower plants in the Plant Kingdom. Mature plants and seedlings are included in the scope of the invention. A mature plant includes a plant at any stage in development beyond the seedling. A seedling is a very young, immature plant in the early stages of development.

Particularly preferred plants are those from: the Family Umbelliferae, particularly of the genera Daucus (particularly the species *carota*, carrot) and Apium (particularly the species *graveolens dulce*, celery) and the like; the Family Solanacea, particularly of the genus Lycopersicon, particularly the species *esculentum* (tomato) and the genus Solanum, particularly the species *tuberosum* (potato) and *melongena* (eggplant), and the like, and the genus Capsicum, particularly the species *annum* (pepper) and the like; and the Family Leguminosae, particularly the genus Glycine, particularly the species *max* (soybean) and the like; and the Family Cruciferae, particularly of the genus Brassica, particularly the species *campestris* (turnip), *oleracea* cv Tastie (cabbage), *oleracea* cv Snowball Y (cauliflower) and *oleracea* cv Emperor (broccoli) and the like; the Family Compositae, particularly the genus Lactuca, and the species *sativa* (lettuce), and the genus Arabidopsis, particularly the species *thaliana* (Thale cress) and the like. Of these Families, the most preferred are the leafy vegetables, for example, the Family Cruciferae, especially the genus Arabidopsis, most especially the species *thaliana*.

ein2 mutant sequences render plants disease and pathogen tolerant, and ethylene insensitive. For purposes of the current invention, disease tolerance is the ability of a plant to survive infection with minimal injury or reduction in the harvested yield of saleable material. Plants with disease tolerance may have extensive levels of infection but have little necrosis and few to no lesions. These plants may also have reduced necrotic and water soaking responses and chlorophyll loss may be virtually absent. In contrast, resistant plants generally limit the growth of pathogens and contain the infection to a localized area with multiple apparent injurious lesions.

The current invention is directed to, for example, identifying plant tolerance to bacterial infections including, but not limited to *Clavibacter michiganense* (formerly *Coynebacterium michiganense*), *Pseudomonas solanacearum* and *Erwinia stewartii*, and more particularly, *Xanthomonas campestris* (specifically pathovars *campestris* and *vesicatoria*), *Pseudomonas syringae* (specifically pathovars *tomato, maculicola*).

In addition to bacterial infections, disease tolerance to infection by other plant pathogens is within the scope of the invention. Examples of viral and fungal pathogens include, but are not limited to tobacco mosaic virus, cauliflower mosaic virus, turnip crinkle virus, turnip yellow mosaic virus; fungi including *Phytophthora infestans, Peronospora parasitica, Rhizoctonia solani, Botrytis cinerea, Phoma lingam* (*Leptosphaeria maculans*), and *Albugo candida*.

Like ein2, ein3 mutants also exhibit ethylene insensitivity. However, ein3 mutants do not exhibit disease or pathogen tolerance. Ethylene, $CH_2=CH_2$, is a naturally occurring plant hormone. The ethylene regulatory pathway includes the ethylene biosynthesis pathway and the ethylene autoregulatory or feedback pathway. In the ethylene biosynthesis pathway, methionine is converted to ethylene with S-adenosylmethionine (SAM) and 1-aminocyclopropane-1-carboxylic acid (ACC) as intermediates. These two reactions are catalyzed by ACC synthase and ethylene-forming enzyme (EFE), respectively. Little is known about the enzymes catalyzing these reactions and their regulation at the molecular level.

The receptor and receptor complex are believed to function with the autoregulatory pathway in the control of ethylene production. Inhibitors of the pathway include AVG (aminoethoxyvinyl-glycine) and AIB ($\alpha$-aminoisobutyric acid).

In accordance with the claimed invention, ethylene insensitive plants are those which are unable to display a typical ethylene response when treated with high concentrations of ethylene. For purposes of the present invention, ethylene insensitivity includes total or partial inability to display a typical ethylene response. A typical ethylene response in wild type plants includes, for example, the so-called "triple response" which involves inhibition of root and stem elongation, radial swelling of the stem, and absence of normal geotropic response (diageotropism). Thus, for example, ethylene insensitive plants may be created in accordance with the present invention by the presence of an altered "triple response" wherein the root and stem are elongated despite the presence of high concentrations of ethylene. Further, a typical ethylene response also includes a shut down or diminution of endogenous ethylene production, upon application of high concentrations of ethylene. Ethylene insensitive plants may thus also be screened for, in accordance with the present invention, by the ability to continue production of ethylene, despite administration of high concentrations of ethylene. Such ethylene insensitive plants are believed to have impaired receptor function such that ethylene is constitutively produced despite the presence of an abundance of exogenous ethylene.

Screening includes screening for root or stem elongation and screening for increased ethylene production. Ethylene sensitive wild type plants experience an inhibition of root and stem elongation when an inhibitory amount of ethylene is administered. By inhibition of root and stem elongation, it is meant that the roots and stems grow less than the normal state (that is, growth without application of an inhibitory amount of ethylene). Typically, normal Arabidopsis (Col) grown without ethylene or ethylene precursor aminocyclopropane, ACC, root elongation is about 6.5±0.2 mm/3 days; normal stem elongation is 8.7±0.3 mm/3 days. In the presence of 100 $\mu$m ACC, Col root growth is 1.5±0.04 mm/3 days and stem growth of 3.2±0.1 mm/3 days for Col. Alternatively, plants may be sprayed with ethaphon or ethrel. By roots, as used here, it is meant mature roots (that is, roots of any plant beyond the rudimentary root of the seedling), as well as roots and root radicles of seedlings. Stems include hypocotyls of immature plants of seedlings and stems, and plant axes of mature plants (that is, any stem beyond the hypocotyl of seedlings).

Ethylene sensitive wild type plants experience a shut down or diminution of endogenous ethylene production, upon application of high concentrations of ethylene. In the ethylene insensitive plants of the present invention, the plants continue endogenous production of ethylene, despite administration of inhibitory amounts of ethylene. An ethylene insensitive plant will produce an amount or have a rate of ethylene production greater than that of a wild type plant upon administration of an inhibitory amount of ethylene. As one skilled in the art will recognize, absolute levels of ethylene produced will change with growth conditions.

Ein1 and ein2 mutants are described for example in, Guzman et al., "Exploiting the Triple Response of Arabidopsis to Identify Ethylene-Related Mutants", *The Plant Cell* 1990, 2, 513, the disclosures of which are hereby incorporated herein by reference, in their entirety.

The present invention is further described in the following example. The example is not to be construed as limiting the scope of the appended claims.

EXAMPLE 1

CLONING AND SEQUENCING OF EIN2

Genomic DNA was isolated from several leaves (2–3) of adult Arabidopsis plants (ecotype Columbia) using a C-TAB DNA miniprep procedure set forth in Doyle, J. J., Doyle, J. L. 1987 Phytochem Buee 19:11–15, incorporated herein by reference in its entirety.

Using specific primers, different fragments of the EIN2 gene covering the complete gene were amplified, see Table 1. The following conditions were used for the PCR amplification: each reaction of 50 µl contained: 50 ng genomic DNA, 20 pmol of each primer, 5 units of taq DNA polymerase, 25 mM MgCl$_2$ and dATP, dCTP, dGTP, dTTP 20 µM each. For the PCR, and ERICOMP PCR thermocycler Twinblok system (Ericomp, Inc., San Diego, Calif.) was used. The PCR conditions were 94° C. for 30 seconds, 54–58° C. (depending on the melting temperature of the primer) 30 seconds, and 72° C. for 1–3 minutes (depending on the expected length of the product).

PCR products were purified from agarose gels using Genclean kitII in accordance with the manufacturer's instructions (Genclean kitII, Bio101, Inc., Vista, Calif.). About 400 ng of the purified DNA was sequenced in an Applied Biosystem automated DNA sequencer (model 373A) (Applied Biosystem Div., Perkin Elmer Corporation, Foster City, Calif.) using dye terminators as recommended by the manufacturer. Each fragment was sequenced several times (4–8) using different genomic DNA minipreps.

TABLE 1

| PCR PRIMERS | EIN2 FRAGMENT AMPLIFIED | SEQUENCING PRIMERS | EIN2 FRAGMENT SEQUENCED |
|---|---|---|---|
| PE24 & PE22 | 268 TO 1718 | PE27 | 638 TO 878 |
| PE25 & PE22 | 916 TO 1718 | PE25 | 958 TO 1428 |
|  |  | PE22 | 1384 TO 1656 |
| PE26 & PE6 | 1160 TO 2528 | PE1 | 1758 TO 2278 |
| PE8 & PE2.7B | 1928 TO 2848 | PE8 | 2058 TO 2358 |
|  |  | PE6 | 2068 TO 2498 |
|  |  | PE14 | 2288 TO 2678 |
|  |  | PB2.7B | 2568 TO 2798 |
| PE2.7A & PE12 | 2698 TO 368 | PE2.7A | 2768 TO 3188 |
|  |  | PE11 | 3018 TO 3228 |
| PE5 & PE16 | 3168 TO 3888 | PE12 | 3208 TO 3608 |
|  |  | PE5 | 3508 TO 3888 |
| PE20 & PE2 | 3938 TO 5568 | PE20 | 3898 TO 4298 |
|  |  | PE4 | 4128 TO 4478 |
|  |  | PE13 | 4497 TO 4739 |
| PE2 & PE4 | 4068 TO 5628 | PE9 | 4811 TO 5144 |
|  |  | PE10A | 5060 TO 5428 |
| PE10A & PE2.5 | 5018 TO 6004 | PE17 | 5478 TO 5753 |
|  |  | PE2.5 | 5633 TO 5933 |

TABLE 2

PRIMERS AND SEQ ID NOS

| SEQUENCE ID NO. | Primer Name | Sequence |
|---|---|---|
| 4 | PE2.7A | GGATCCTCTAGTCAAATTACCGC |
| 5 | PE2.7B | AGATCTGGTATATTCCGTCTGCAC |
| 6 | PE2.5 | CCGGATTCGGTTTGTAGC |
| 7 | PE2 | GAAAGCCACATCACCTGC |
| 8 | PE4 | GACACCGGGAAGTATCG |
| 9 | PE5 | CTGCTTTCATAGAAGAGGC |
| 10 | PE6 | GTCAGAACAAACCTGCTCC |
| 11 | PE8 | GGCCGCCATGGATGCA |
| 12 | PE10A | CTTGAAGGATCCGAGTGG |
| 13 | PE12 | CTTGCTGTTATTCTCCATGC |
| 14 | PE16 | CTGGCTGGCAGCCACGCC |
| 15 | PE20 | TGGTTGCTGAAGCCAGGG |
| 16 | PE22 | ATGCCCAAGAACATGCACG |
| 17 | PE24 | GTTGTTAGGTCAACTTGCG |
| 18 | PE25 | CTCTGTTAGGGCTTCCTCC |
| 19 | PE26 | GAATCAGATTTCGCGAGG |

Primer sequences are set forth 5' to 3'.

EXAMPLE 2

CREATION OF ETHYLENE INSENSITIVE PLANTS USING *ARABIDOPSIS THALIANA* COL-O ETHYLENE INSENSITIVE2 COMPLEMENTARY DNA

An EIN2 complementary DNA clone called pcEIN2 containing the full length coding region plus 580 base pairs of the 5' end and 300 base pairs of the 3' end of untranslated region was subcloned in the plant transformation vector pKYLX7 to generate a plasmid called pKYLX7:cEIN2. The pKYLX7 vector contains the 35S promoter of the cauliflower mosaic virus and the rbcS-E9 polyadenylation site allowing for the expression of genes in plants (Schardl, C. L., et al., 1987 "Design and construction of a versatile system for the expression of foreign genes in plants" *Gene*, 61:1–11). The pKYLX7:cEIN2 plasmid was introduced into Agrobacterium tumefaciens cells (strain C58C1) by electroporation, and the bacterial transformants were selected on LB plates containing kanamycin. Agrobacterium cells carrying the pKYLX7:cEIN2 plasmid or the pKYLX7 plasmid alone were used to infect *Arabidopsis thaliana* ecotype Columbia plants using the vacuum infiltration procedure (Bechtold et al., 1993 "In planta Agrobacterium-mediated transfer by infiltration of adult *Arabidopsis thaliana* plants" *Comptes rendus de Academic des Sciences* 316, 1194–1199). After further growth of the infiltrated plants, seeds (T1 generation) were collected and plated on MS medium supplemented with 1% sucrose and 50 µg/ml kanamycin. Plant lines resistant to kanamycin were selected and transferred to soil for further growth. Seeds (T2 generation) were harvested from the individual T1 plants.

Figure 2A:
FIGS. 2A–2B displays *Arabidopsis thaliana* plants grown in air or ethylene.
Figure 2B:

In order to study the effect of the pKYLX7:cEIN2 on the ethylene responses in these plants, transformed plants at the seedling stage were examined for the presence of the ethylene-mediated triple response phenotype (Guzman and Ecker, 1990 "Exploiting the triple response of Arabidopsis to identify ethylene-related mutants", *Plant Cell* 2, 513–523). T2 generation seedlings were plated on MS medium supplemented with 1% sucrose and were germinated and grown in the dark for 3 days in the presence or absence of 10 µl of ethylene/liter of air. Seeds corresponding to 207 T1 independent transformed lines were examined. In six of the transgenic pKYLX7:cEIN2-containing plants, plants were found that showed a strong ethylene insensitive (Ein-) phenotype (FIGS. 2A and 2B). This effect was heritable in subsequent generations and the ethylene insensitivity has not been observed in a similar number of plant lines transformed with the pKYLX plasmid alone. Therefore, the Arabidopsis cEIN2 cDNA can be used to create a plant that is resistant to the effects of ethylene. This approach to the creation of ethylene insensitive plants can be applied to any plant that contains a gene homologous to EIN2.

The disclosures of each patent, patent application and publication cited or described in this document are hereby incorporated herein by reference, in their entirety.

Various modifications of the invention in addition to those shown and described herein will be apparent to those skilled in the art from the foregoing description. Such modifications are also intended to fall within the scope of the appended claims.

What is claimed is:

1. An isolated nucleic acid molecule comprising a nucleic acid molecule selected from the group consisting of SEQ ID NOS: 1 and 2.

2. An isolated DNA molecule comprising a sequence complementary to the isolated nucleic acid molecule of claim 1.

3. An isolated DNA molecule comprising a sequence complementary to an isolated nucleic acid molecule selected from the group consisting of SEQ ID NOS: 1 and 2.

4. A transformed plant cell comprising a nucleic acid molecule selected from the group consisting of SEQ ID NOS: 1 and 2.

5. A transgenic plant comprising a nucleic acid molecule selected from the group consisting of SEQ ID NOS: 1 and 2.

* * * * *

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
      (A) LENGTH: 6172 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

```
TAATAAAGGT GGGGTGAAGA AACCAAATGT TTAACCTGGA AAATTTATTT TAAAAGACGT      60

TTTTTTAGCT ATAAGAAAAA AAAGGATAAT ACCCTTATTT TTACATGTTA TTTACCAGTA     120

ATAATTTTTT TTTTCTCTCT CTCTCTTTGA AGGTGGCACG AGCACCCATA ACCTTCAGAC     180

CTATAGATAC AAATATGTAT GTATACGTTT TTTATATATA AATATTTTAT ATAATTGATT     240

TTTCGATCTT CTTTTATCTC TCTCTTTCGA TGGAACTGAG CTCTTTCTCT CTTTCCTCTT     300

CTTTTCTCTC TCTATCTCTA TCTCTCGTAG CTTGATAAGA GTTTCTCTCT TTTGAAGATC     360

CGTTTCTCTC TCTCTCACTG AGACTATTGT TGTTAGGTCA ACTTGCGATC ATGGCGATTT     420

CGAAGGTGAC TTCTTTCAAA AACCCTAATC CTCTGTTTTT TTTTTTATTT TGCTGGGGGG     480

CTTTGTACGG ACTTTCATGG GTTTTTGTAG CTTTTCCCTC GGCTTTTGCG CAAATGAGAC     540

TTTCTGGGTT TTTTTTCCAG CTTTTTATAA TTTCATCAGG TGGATCGAAT TCGTAGTTTC     600

AGCTTAGATC TCTCTCCCTC TTCATTATCT GGACTTTCCA GACTTGGAGT TCTTCGGGAT     660

TGTTTTCGGT TTCTGGGTTT TGTTTTAATT GCGAGATTTA AGCTTTTTTC TTTTTTACTA     720

CTGTACTTGG TTTGTGGTTG ACCTTTTTTT TCCTTGAAGA TCTGAATGCG TAGATCATAC     780

GGGATCTTTG CATTTTTGTT GCTTTTCGTC AGCGTTACGA TTCTTTTAGC TTCAGTTTAG     840

TTGAAATTTG TATTTTTTTT GAGCTTATCT TCTTTTTGTT GCTGCTTCAT ACTAAGATCA     900

ATTATTGATT TGTAATACTA CTGTATCTGA AGATTTTCAC CATAAAAAAA AAATTCAGGT     960

CTGAAGCTGA TTTCGAATGG TTTGGAGATA TCCGTAGTGG TTAAGCATAT GGAAGTCTAT    1020

GTTCTGCTCT TGGTTGCTCT GTTAGGGCTT CCTCCATTTG GACCAACTTA GCTGAATGTT    1080

GTATGATCTC TCTCCTTGAA GCAGCAAATA AGAAGAAGGT CTGGTCCTTA ACTTAACATC    1140

TGGTTACTAG AGGAAACTTC AGCTATTATT AGGTAAAGAA AGACTGTACA GAGTTGTATA    1200

ACAAGTAAGC GTTAGAGTGG CTTTGTTTGC CTCGGTGATA GAAGAACCGA CTGATTCGTT    1260

GTTGTGTGTT AGCTTTGGAG GGAATCAGAT TTCGCGAGGG AAGGTGTTTT AGATCAAATC    1320

TGTGAATTTT ACTCAACTGA GGCTTTTAGT GAACCACGAC TGTAGAGTTG ACCTTGAATC    1380

CTACTCTGAG TAATTATATT ATCAGATAGA TTTAGGATGG AAGCTGAAAT TGTGAATGTG    1440

AGACCTCAGC TAGGGTTTAT CCAGAGAATG GTTCCTGCTC TACTTCCTGT CCTTTTGGTT    1500
```

-continued

```
TCTGTCGGAT ATATTGATCC CGGGAAATGG GTTGCAAATA TCGAAGGAGG TGCTCGTTTC    1560

GGGTATGACT TGGTGGCAAT TACTCTGCTT TTCAATTTTG CCGCCATCTT ATGCCAATAT    1620

GTTGCAGCTC GCATAAGCGT TGTGACTGGT AAACACTTGG CTCAGGTAAA CATTTTTCTG    1680

ATCTCTAAAG AACAAACTTT TTAAAATAAC AAACTGGGCT CTGTGGTTGT CTTGTCACTT    1740

TCTCAAAGTG GAATTCTACT AACCACCTTC TCTATTTTTC TAACATTTTA ATGTTCTTTA    1800

CTGGGACAGA TCTGCAATGA AGAATATGAC AAGTGGACGT GCATGTTCTT GGGCATTCAG    1860

GCGGAGTTCT CAGCAATTCT GCTCGACCTT ACCATGGTAG TTACTTACAA TCTTTGCTGT    1920

TCTTAATTTT TTTATTATGT GATAAAATTT TGATTCCTCT GACTTGAGCT TCTCTATTAT    1980

AAACAGGTTG TGGGAGTTGC GCATGCACTT AACCTTTTGT TTGGGGTGGA GTTATCCACT    2040

GGAGTGTTTT TGGCCGCCAT GGATGCGTTT TTATTTCCTG TTTTCGCCTC TTTCCTTGTA    2100

TGACTGGTCT TCCTGTCTTG TTTTTTTTCT CCACGTTCTT GAAATAGCAT TATTGGAAAT    2160

TAGCTGACAT GCATACAATT TCTGACAGGA AAATGGTATG GCAAATACAG TATCCATTTA    2220

CTCTGCAGGC CTGGTATTAC TTCTCTATGT ATCTGGCGTC TTGCTGAGTC AGTCTGAGAT    2280

CCCACTCTCT ATGAATGGAG TGTTAACTCG GTTAAATGGA GAGAGCGCAT TCGCACTGAT    2340

GGGTCTTCTT GGCGCAAGCA TCGTCCCTCA CAATTTTTAT ATCCATTCTT ATTTTGCTGG    2400

GGTACCTTTT TTCTCTTTAT ATGTATCTCT CTTTTCTGTT AAGAAGCAAT AATTATACTA    2460

AGCAGTGAAC GCTCTATTAC AGGAAAGTAC ATCTTCGTCT GATGTCGACA AGAGCAGCTT    2520

GTGTCAAGAC CATTTGTTCG CCATCTTTGG TGTCTTCAGC GGACTGTCAC TTGTAAATTA    2580

TGTATTGATG AATGCAGCAG CTAATGTGTT TCACAGTACT GGCCTTGTGG TACTGACTTT    2640

TCACGATGCC TTGTCACTAA TGGAGCAGGT TTGTTCTGAC GGTTTTATGT TCGTATTAGT    2700

CTATAATTCA TTTTTAGGGA AAATGTTCAG AAATCTCTCG TGATTATTAA TTATCTTGTT    2760

CTTGATTGTT GATCACAGGT ATTTATGAGT CCGCTCATTC CAGTGGTCTT TTTGATGCTC    2820

TTGTTCTTCT CTAGTCAAAT TACCGCACTA GCTTGGGCTT TCGGTGGAGA GGTCGTCCTG    2880

CATGACTTCC TGAAGATAGA AATACCCGCT TGGCTTCATC GTGCTACAAT CAGAATTCTT    2940

GCAGTTGCTC CTGCGCTTTA TTGTGTATGG ACATCTGGTG CAGACGGAAT ATACCAGTTA    3000

CTTATATTCA CCCAGGTCTT GGTGGCAATG ATGCTTCCTT GCTCGGTAAT ACCGCTTTTC    3060

CGCATTGCTT CGTCGAGACA AATCATGGGT GTCCATAAAA TCCCTCAGGT TGGCGAGTTC    3120

CTCGCACTTA CAACGTTTTT GGGATTTCTG GGGTTGAATT TGTTTTTGT TGTTGAGATG     3180

GTATTTGGGA GCAGTGACTG GGCTGGTGGT TTGAGATGGA ATACCGTGAT GGGCACCTCG    3240

ATTCAGTACA CCACTCTGCT TGTATCGTCA TGTGCATCCT TATGCCTGAT ACTCTGGCTG    3300

GCAGCCACGC CGCTGAAATC TGCGAGTAAC AGAGCGGAAG CTCAAATATG AACATGGAT     3360

GCTCAAAATG CTTTATCTTA TCCATCTGTT CAAGAAGAGG AAATTGAAAG AACAGAAACA    3420

AGGAGGAACG AAGACGAATC AATAGTGCGG TTGGAAAGCA GGGTAAAGGA TCAGTTGGAT    3480

ACTACGTCTG TTACTAGCTC GGTCTATGAT TTGCCAGAGA ACATTCTAAT GACGGATCAA    3540

GAAATCCGTT CGAGCCCTCC AGAGGAAAGA GAGTTGGATG TAAAGTACTC TACCTCTCAA    3600

GTTAGTAGTC TTAAGGAAGA CTCTGATGTA AAGGAACAGT CTGTATTGCA GTCAACAGTG    3660

GTTAATGAGG TCAGTGATAA GGATCTGATT GTTGAAACAA AGATGGCGAA AATTGAACCA    3720

ATGAGTCCTG TGGAGAAGAT TGTTAGCATG GAGAATAACA GCAAGTTTAT TGAAAAGGAT    3780

GTTGAAGGGG TTTCATGGGA AACAGAAGAA GCTACCAAAG CTGCTCCTAC AAGCAACTTT    3840

ACTGTCGGAT CTGATGGTCC TCCTTCATTC CGCAGCTTAA GTGGGGAAGG GGGAAGTGGG    3900
```

```
ACTGGAAGCC TTTCACGGTT GCAAGGTTTG GGACGTGCTG CCCGGAGACA CTTATCTGCG    3960

ATCCTTGATG AATTTTGGGG ACATTTATAT GATTTTCATG GGCAATTGGT TGCTGAAGCC    4020

AGGGCAAAGA AACTAGATCA GCTGTTTGGC ACTGATCAAA AGTCAGCCTC TTCTATGAAA    4080

GCAGATTCGT TTGGAAAAGA CATTAGCAGT GGATATTGCA TGTCACCAAC TGCGAAGGGA    4140

ATGGATTCAC AGATGACTTC AAGTTTATAT GATTCACTGA AGCAGCAGAG GACACCGGGA    4200

AGTATCGATT CGTTGTATGG ATTACAAAGA GGTTCGTCAC CGTCACCGTT GGTCAACCGT    4260

ATGCAGATGT TGGGTGCATA TGGTAACACC ACTAATAATA ATAATGCTTA CGAATTGAGT    4320

GAGAGAAGAT ACTCTAGCCT GCGTGCTCCA TCATCTTCAG AGGGTTGGGA ACACCAACAA    4380

CCAGCTACAG TTCACGGATA CCAGATGAAG TCATATGTAG ACAATTTGGC AAAAGAAAGG    4440

CTTGAAGCCT ACAATCCCG TGGAGAGATC CCGACATCGA GATCTATGGC GCTTGGTACA    4500

TTGAGCTATA CACAGCAACT TGCTTTAGCC TTGAAACAGA AGTCCCAGAA TGGTCTAACC    4560

CCTGGACCAG CTCCTGGGTT TGAGAATTTT GCTGGGTCTA AAGCATATC GCGACAATCT    4620

GAAAGATCTT ATTACGGTGT TCCATCTTCT GGCAATACTG ATACTGTTGG CGCAGCAGTA    4680

GCCAATGAGA AAAATATAG TAGCATGCCA GATATCTCAG GATTGTCTAT GTCCGCAAGG    4740

AACATGCATT TACCAAACAA CAAGAGTGGA TACTGGGATC CGTCAAGTGG AGGAGGAGGG    4800

TATGGTGCGT CTTATGGTCG GTTAAGCAAT GAATCATCGT TATATTCTAA TTTGGGGTCA    4860

CGGGTGGGAG TACCCTCGAC TTATGATGAC ATTTCTCAAT CAAGAGGAGG CTACAGAGAT    4920

GCCTACAGTT TGCCACAGAG TGCAACAACA GGGACCGGAT CGCTTTGGTC CAGACAGCCC    4980

TTTGAGCAGT TTGGTGTAGC GGAGAGGAAT GGTGCTGTTG GTGAGGAGCT CAGGAATAGA    5040

TCGAATCCGA TCAATATAGA CAACAACGCT TCTTCTAATG TTGATGCAGA GGCTAAGCTT    5100

CTTCAGTCGT TCAGGCACTG TATTCTAAAG CTTATTAAAC TTGAAGGATC CGAGTGGTTG    5160

TTTGGACAAA GCGATGGAGT TGATGAAGAA CTGATTGACC GGGTAGCTGC ACGAGAGAAG    5220

TTTATCTATG AAGCTGAAGC TCGAGAAATA AACCAGGTGG GTCACATGGG GGAGCCACTA    5280

ATTTCATCGG TTCCTAACTG TGGAGATGGT TGCGTTTGGA GAGCTGATTT GATTGTGAGC    5340

TTTGGAGTTT GGTGCATTCA CCGTGTCCTT GACTTGTCTC TCATGGAGAG TCGGCCTGAG    5400

CTTTGGGGAA AGTACACTTA CGTTCTCAAC CGCCTACAGG TAACAAAAAC CGCAGTAGTT    5460

CATTGAAAAT CACAGTTTTG CAGTTTGAAA ATATTGACAT GTATGGATTT AAACAGGGAG    5520

TGATTGATCC GGCGTTCTCA AAGCTGCGGA CACCAATGAC ACCGTGCTTT TGCCTTCAGA    5580

TTCCAGCGAG CCACCAGAGA GCGAGTCCGA CTTCAGCTAA CGGAATGTTA CCTCCGGCTG    5640

CAAAACCGGC TAAAGGCAAA TGCACAACCG CAGTCACACT TCTTGATCTA ATCAAAGACG    5700

TTGAAATGGC AATCTCTTGT AGAAAAGGCC GAACCGGTAC AGCTGCAGGT GATGTGGCTT    5760

TCCCAAAGGG GAAAGAGAAT TTGGCTTCGG TTTTGAAGCG GTATAAACGT CGGTTATCGA    5820

ATAAACCAGT AGGTATGAAT CAGGATGGAC CCGGTTCAAG AAAAAACGTG ACTGCGTACG    5880

GATCATTGGG TTGAAGAAGA AGAACATTGT GAGAAATCTC ATGATCAAAG TGACGTCGAG    5940

AGGGAAGCCG AAGAATCAAA ACTCTCGCTT TTGATTGCTC CTCTGCTTCG TTAATTGTGT    6000

ATTAAGAAAA GAAGAAAAAA AATGGATTTT TGTTGCTTCA GAATTTTTCG CTCTTTTTTT    6060

CTTAATTTGG TTGTAATGTT ATGTTTATAT ACATATATCA TCATCATAGG ACCATAGCTA    6120

CAAACCGAAT CCGGTTTGTG TAATTCTATG CGGAATCATA AAGAAATCGT CG            6172
```

(2) INFORMATION FOR SEQ ID NO:2:

(i) SEQUENCE CHARACTERISTICS:
    (A) LENGTH: 4746 base pairs
    (B) TYPE: nucleic acid
    (C) STRANDEDNESS: single
    (D) TOPOLOGY: linear (ii) MOLECULE TYPE: RNA (genomic)

(iii) HYPOTHETICAL: NO (iv) ANTI-SENSE: NO (ix) FEATURE:
    (A) NAME/KEY: CDS
    (B) LOCATION: 584..4468

(xi) SEQUENCE DESCRIPTION: SEQ ID NO:2:

```
CTTTTCTCTC TCTATCTCTA TCTCTCGTAG CTTGATAAGA GTTTCTCTCT TTTGAAGATC      60

CGTTTCTCTC TCTCTCACTG AGACTATTGT TGTTAGGTCA ACTTGCGATC ATGGCGATTT     120

CGAAGGTCTG AAGCTGATTT CGAATGGTTT GGAGATATCC GTAGTGGTTA AGCATATGGA     180

AGTCTATGTT CTGCTCTTGG TTGCTCTGTT AGGGCTTCCT CCATTTGGAC CAACTTAGCT     240

GAATGTTGTA TGATCTCTCT CCTTGAAGCA GCAAATAAGA AGAAGGTCTG GTCCTTAACT     300

TAACATCTGG TTACTAGAGG AAACTTCAGC TATTATTAGG TAAAGAAAGA CTGTACAGAG     360

TTGTATAACA AGTAAGCGTT AGAGTGGCTT TGTTTGCCTC GGTGATAGAA GAACCGACTG     420

ATTCGTTGTT GTGTGTTAGC TTTGGAGGGA ATCAGATTTC GCGAGGGAAG GTGTTTTAGA     480

TCAAATCTGT GAATTTTACT CAACTGAGGC TTTTAGTGAA CCACGACTGT AGAGTTGACC     540

TTGAATCCTA CTCTGAGTAA TTATATTATC AGATAGATTT AGG ATG GAA GCT GAA     595
                                              Met Glu Ala Glu
                                              1

ATT GTG AAT GTG AGA CCT CAG CTA GGG TTT ATC CAG AGA ATG GTT CCT      643
Ile Val Asn Val Arg Pro Gln Leu Gly Phe Ile Gln Arg Met Val Pro
  5                  10                  15                  20

GCT CTA CTT CCT GTC CTT TTG GTT TCT GTC GGA TAT ATT GAT CCC GGG      691
Ala Leu Leu Pro Val Leu Leu Val Ser Val Gly Tyr Ile Asp Pro Gly
              25                  30                  35

AAA TGG GTT GCA AAT ATC GAA GGA GGT GCT CGT TTC GGG TAT GAC TTG      739
Lys Trp Val Ala Asn Ile Glu Gly Gly Ala Arg Phe Gly Tyr Asp Leu
          40                  45                  50

GTG GCA ATT ACT CTG CTT TTC AAT TTT GCC GCC ATC TTA TGC CAA TAT      787
Val Ala Ile Thr Leu Leu Phe Asn Phe Ala Ala Ile Leu Cys Gln Tyr
      55                  60                  65

GTT GCA GCT CGC ATA AGC GTT GTG ACT GGT AAA CAC TTG GCT CAG ATC      835
Val Ala Ala Arg Ile Ser Val Val Thr Gly Lys His Leu Ala Gln Ile
  70                  75                  80

TGC AAT GAA GAA TAT GAC AAG TGG ACG TGC ATG TTC TTG GGC ATT CAG      883
Cys Asn Glu Glu Tyr Asp Lys Trp Thr Cys Met Phe Leu Gly Ile Gln
 85                  90                  95                 100

GCG GAG TTC TCA GCA ATT CTG CTC GAC CTT ACC ATG GTT GTG GGA GTT      931
Ala Glu Phe Ser Ala Ile Leu Leu Asp Leu Thr Met Val Val Gly Val
              105                 110                 115

GCG CAT GCA CTT AAC CTT TTG TTT GGG GTG GAG TTA TCC ACT GGA GTG      979
Ala His Ala Leu Asn Leu Leu Phe Gly Val Glu Leu Ser Thr Gly Val
          120                 125                 130

TTT TTG GCC GCC ATG GAT GCG TTT TTA TTT CCT GTT TTC GCC TCT TTC     1027
Phe Leu Ala Ala Met Asp Ala Phe Leu Phe Pro Val Phe Ala Ser Phe
      135                 140                 145

CTT GAA AAT GGT ATG GCA AAT ACA GTA TCC ATT TAC TCT GCA GGC CTG     1075
Leu Glu Asn Gly Met Ala Asn Thr Val Ser Ile Tyr Ser Ala Gly Leu
 150                 155                 160
```

```
GTA TTA CTT CTC TAT GTA TCT GGC GTC TTG CTG AGT CAG TCT GAG ATC        1123
Val Leu Leu Leu Tyr Val Ser Gly Val Leu Leu Ser Gln Ser Glu Ile
165             170                 175                 180

CCA CTC TCT ATG AAT GGA GTG TTA ACT CGG TTA AAT GGA GAG AGC GCA        1171
Pro Leu Ser Met Asn Gly Val Leu Thr Arg Leu Asn Gly Glu Ser Ala
                185                 190                 195

TTC GCA CTG ATG GGT CTT CTT GGC GCA AGC ATC GTC CCT CAC AAT TTT        1219
Phe Ala Leu Met Gly Leu Leu Gly Ala Ser Ile Val Pro His Asn Phe
            200                 205                 210

TAT ATC CAT TCT TAT TTT GCT GGG GAA AGT ACA TCT TCG TCT GAT GTC        1267
Tyr Ile His Ser Tyr Phe Ala Gly Glu Ser Thr Ser Ser Ser Asp Val
        215                 220                 225

GAC AAG AGC AGC TTG TGT CAA GAC CAT TTG TTC GCC ATC TTT GGT GTC        1315
Asp Lys Ser Ser Leu Cys Gln Asp His Leu Phe Ala Ile Phe Gly Val
    230                 235                 240

TTC AGC GGA CTG TCA CTT GTA AAT TAT GTA TTG ATG AAT GCA GCA GCT        1363
Phe Ser Gly Leu Ser Leu Val Asn Tyr Val Leu Met Asn Ala Ala Ala
245                 250                 255                 260

AAT GTG TTT CAC AGT ACT GGC CTT GTG GTA CTG ACT TTT CAC GAT GCC        1411
Asn Val Phe His Ser Thr Gly Leu Val Val Leu Thr Phe His Asp Ala
                265                 270                 275

TTG TCA CTA ATG GAG CAG GTA TTT ATG AGT CCG CTC ATT CCA GTG GTC        1459
Leu Ser Leu Met Glu Gln Val Phe Met Ser Pro Leu Ile Pro Val Val
            280                 285                 290

TTT TTG ATG CTC TTG TTC TTC TCT AGT CAA ATT ACC GCA CTA GCT TGG        1507
Phe Leu Met Leu Leu Phe Phe Ser Ser Gln Ile Thr Ala Leu Ala Trp
        295                 300                 305

GCT TTC GGT GGA GAG GTC GTC CTG CAT GAC TTC CTG AAG ATA GAA ATA        1555
Ala Phe Gly Gly Glu Val Val Leu His Asp Phe Leu Lys Ile Glu Ile
    310                 315                 320

CCC GCT TGG CTT CAT CGT GCT ACA ATC AGA ATT CTT GCA GTT GCT CCT        1603
Pro Ala Trp Leu His Arg Ala Thr Ile Arg Ile Leu Ala Val Ala Pro
325                 330                 335                 340

GCG CTT TAT TGT GTA TGG ACA TCT GGT GCA GAC GGA ATA TAC CAG TTA        1651
Ala Leu Tyr Cys Val Trp Thr Ser Gly Ala Asp Gly Ile Tyr Gln Leu
                345                 350                 355

CTT ATA TTC ACC CAG GTC TTG GTG GCA ATG ATG CTT CCT TGC TCG GTA        1699
Leu Ile Phe Thr Gln Val Leu Val Ala Met Met Leu Pro Cys Ser Val
            360                 365                 370

ATA CCG CTT TTC CGC ATT GCT TCG TCG AGA CAA ATC ATG GGT GTC CAT        1747
Ile Pro Leu Phe Arg Ile Ala Ser Ser Arg Gln Ile Met Gly Val His
        375                 380                 385

AAA ATC CCT CAG GTT GGC GAG TTC CTC GCA CTT ACA ACG TTT TTG GGA        1795
Lys Ile Pro Gln Val Gly Glu Phe Leu Ala Leu Thr Thr Phe Leu Gly
    390                 395                 400

TTT CTG GGG TTG AAT GTT GTT TTT GTT GTT GAG ATG GTA TTT GGG AGC        1843
Phe Leu Gly Leu Asn Val Val Phe Val Val Glu Met Val Phe Gly Ser
405                 410                 415                 420

AGT GAC TGG GCT GGT GGT TTG AGA TGG AAT ACC GTG ATG GGC ACC TCG        1891
Ser Asp Trp Ala Gly Gly Leu Arg Trp Asn Thr Val Met Gly Thr Ser
                425                 430                 435

ATT CAG TAC ACC ACT CTG CTT GTA TCG TCA TGT GCA TCC TTA TGC CTG        1939
Ile Gln Tyr Thr Thr Leu Leu Val Ser Ser Cys Ala Ser Leu Cys Leu
            440                 445                 450

ATA CTC TGG CTG GCA GCC ACG CCG CTG AAA TCT GCG AGT AAC AGA GCG        1987
Ile Leu Trp Leu Ala Ala Thr Pro Leu Lys Ser Ala Ser Asn Arg Ala
        455                 460                 465

GAA GCT CAA ATA TGG AAC ATG GAT GCT CAA AAT GCT TTA TCT TAT CCA        2035
Glu Ala Gln Ile Trp Asn Met Asp Ala Gln Asn Ala Leu Ser Tyr Pro
    470                 475                 480
```

-continued

| | | | | | | | | | | | | | | |
|---|---|---|---|---|---|---|---|---|---|---|---|---|---|---|
| TCT | GTT | CAA | GAA | GAG | GAA | ATT | GAA | AGA | ACA | GAA | ACA | AGG | AGG | AAC | GAA | 2083
| Ser | Val | Gln | Glu | Glu | Glu | Ile | Glu | Arg | Thr | Glu | Thr | Arg | Arg | Asn | Glu |
| 485 | | | | 490 | | | | | 495 | | | | | 500 | |

```
GAC GAA TCA ATA GTG CGG TTG GAA AGC AGG GTA AAG GAT CAG TTG GAT    2131
Asp Glu Ser Ile Val Arg Leu Glu Ser Arg Val Lys Asp Gln Leu Asp
                    505                 510                 515

ACT ACG TCT GTT ACT AGC TCG GTC TAT GAT TTG CCA GAG AAC ATT CTA    2179
Thr Thr Ser Val Thr Ser Ser Val Tyr Asp Leu Pro Glu Asn Ile Leu
                520                 525                 530

ATG ACG GAT CAA GAA ATC CGT TCG AGC CCT CCA GAG GAA AGA GAG TTG    2227
Met Thr Asp Gln Glu Ile Arg Ser Ser Pro Pro Glu Glu Arg Glu Leu
            535                 540                 545

GAT GTA AAG TAC TCT ACC TCT CAA GTT AGT AGT CTT AAG GAA GAC TCT    2275
Asp Val Lys Tyr Ser Thr Ser Gln Val Ser Ser Leu Lys Glu Asp Ser
        550                 555                 560

GAT GTA AAG GAA CAG TCT GTA TTG CAG TCA ACA GTG GTT AAT GAG GTC    2323
Asp Val Lys Glu Gln Ser Val Leu Gln Ser Thr Val Val Asn Glu Val
565                 570                 575                 580

AGT GAT AAG GAT CTG ATT GTT GAA ACA AAG ATG GCG AAA ATT GAA CCA    2371
Ser Asp Lys Asp Leu Ile Val Glu Thr Lys Met Ala Lys Ile Glu Pro
                    585                 590                 595

ATG AGT CCT GTG GAG AAG ATT GTT AGC ATG GAG AAT AAC AGC AAG TTT    2419
Met Ser Pro Val Glu Lys Ile Val Ser Met Glu Asn Asn Ser Lys Phe
                600                 605                 610

ATT GAA AAG GAT GTT GAA GGG GTT TCA TGG GAA ACA GAA GAA GCT ACC    2467
Ile Glu Lys Asp Val Glu Gly Val Ser Trp Glu Thr Glu Glu Ala Thr
            615                 620                 625

AAA GCT GCT CCT ACA AGC AAC TTT ACT GTC GGA TCT GAT GGT CCT CCT    2515
Lys Ala Ala Pro Thr Ser Asn Phe Thr Val Gly Ser Asp Gly Pro Pro
        630                 635                 640

TCA TTC CGC AGC TTA AGT GGG GAA GGG GGA AGT GGG ACT GGA AGC CTT    2563
Ser Phe Arg Ser Leu Ser Gly Glu Gly Gly Ser Gly Thr Gly Ser Leu
645                 650                 655                 660

TCA CGG TTG CAA GGT TTG GGA CGT GCT GCC CGG AGA CAC TTA TCT GCG    2611
Ser Arg Leu Gln Gly Leu Gly Arg Ala Ala Arg Arg His Leu Ser Ala
                    665                 670                 675

ATC CTT GAT GAA TTT TGG GGA CAT TTA TAT GAT TTT CAT GGG CAA TTG    2659
Ile Leu Asp Glu Phe Trp Gly His Leu Tyr Asp Phe His Gly Gln Leu
                680                 685                 690

GTT GCT GAA GCC AGG GCA AAG AAA CTA GAT CAG CTG TTT GGC ACT GAT    2707
Val Ala Glu Ala Arg Ala Lys Lys Leu Asp Gln Leu Phe Gly Thr Asp
            695                 700                 705

CAA AAG TCA GCC TCT TCT ATG AAA GCA GAT TCG TTT GGA AAA GAC ATT    2755
Gln Lys Ser Ala Ser Ser Met Lys Ala Asp Ser Phe Gly Lys Asp Ile
        710                 715                 720

AGC AGT GGA TAT TGC ATG TCA CCA ACT GCG AAG GGA ATG GAT TCA CAG    2803
Ser Ser Gly Tyr Cys Met Ser Pro Thr Ala Lys Gly Met Asp Ser Gln
725                 730                 735                 740

ATG ACT TCA AGT TTA TAT GAT TCA CTG AAG CAG CAG AGG ACA CCG GGA    2851
Met Thr Ser Ser Leu Tyr Asp Ser Leu Lys Gln Gln Arg Thr Pro Gly
                    745                 750                 755

AGT ATC GAT TCG TTG TAT GGA TTA CAA AGA GGT TCG TCA CCG TCA CCG    2899
Ser Ile Asp Ser Leu Tyr Gly Leu Gln Arg Gly Ser Ser Pro Ser Pro
                760                 765                 770

TTG GTC AAC CGT ATG CAG ATG TTG GGT GCA TAT GGT AAC ACC ACT AAT    2947
Leu Val Asn Arg Met Gln Met Leu Gly Ala Tyr Gly Asn Thr Thr Asn
            775                 780                 785

AAT AAT AAT GCT TAC GAA TTG AGT GAG AGA AGA TAC TCT AGC CTG CGT    2995
Asn Asn Asn Ala Tyr Glu Leu Ser Glu Arg Arg Tyr Ser Ser Leu Arg
        790                 795                 800
```

```
GCT CCA TCA TCT TCA GAG GGT TGG GAA CAC CAA CAA CCA GCT ACA GTT    3043
Ala Pro Ser Ser Ser Glu Gly Trp Glu His Gln Gln Pro Ala Thr Val
805             810                 815                 820

CAC GGA TAC CAG ATG AAG TCA TAT GTA GAC AAT TTG GCA AAA GAA AGG    3091
His Gly Tyr Gln Met Lys Ser Tyr Val Asp Asn Leu Ala Lys Glu Arg
                825                 830                 835

CTT GAA GCC TTA CAA TCC CGT GGA GAG ATC CCG ACA TCG AGA TCT ATG    3139
Leu Glu Ala Leu Gln Ser Arg Gly Glu Ile Pro Thr Ser Arg Ser Met
            840                 845                 850

GCG CTT GGT ACA TTG AGC TAT ACA CAG CAA CTT GCT TTA GCC TTG AAA    3187
Ala Leu Gly Thr Leu Ser Tyr Thr Gln Gln Leu Ala Leu Ala Leu Lys
        855                 860                 865

CAG AAG TCC CAG AAT GGT CTA ACC CCT GGA CCA GCT CCT GGG TTT GAG    3235
Gln Lys Ser Gln Asn Gly Leu Thr Pro Gly Pro Ala Pro Gly Phe Glu
    870                 875                 880

AAT TTT GCT GGG TCT AGA AGC ATA TCG CGA CAA TCT GAA AGA TCT TAT    3283
Asn Phe Ala Gly Ser Arg Ser Ile Ser Arg Gln Ser Glu Arg Ser Tyr
885                 890                 895                 900

TAC GGT GTT CCA TCT TCT GGC AAT ACT GAT ACT GTT GGC GCA GCA GTA    3331
Tyr Gly Val Pro Ser Ser Gly Asn Thr Asp Thr Val Gly Ala Ala Val
                905                 910                 915

GCC AAT GAG AAA AAA TAT AGT AGC ATG CCA GAT ATC TCA GGA TTG TCT    3379
Ala Asn Glu Lys Lys Tyr Ser Ser Met Pro Asp Ile Ser Gly Leu Ser
            920                 925                 930

ATG TCC GCA AGG AAC ATG CAT TTA CCA AAC AAC AAG AGT GGA TAC TGG    3427
Met Ser Ala Arg Asn Met His Leu Pro Asn Asn Lys Ser Gly Tyr Trp
        935                 940                 945

GAT CCG TCA AGT GGA GGA GGA GGG TAT GGT GCG TCT TAT GGT CGG TTA    3475
Asp Pro Ser Ser Gly Gly Gly Gly Tyr Gly Ala Ser Tyr Gly Arg Leu
    950                 955                 960

AGC AAT GAA TCA TCG TTA TAT TCT AAT TTG GGG TCA CGG GTG GGA GTA    3523
Ser Asn Glu Ser Ser Leu Tyr Ser Asn Leu Gly Ser Arg Val Gly Val
965                 970                 975                 980

CCC TCG ACT TAT GAT GAC ATT TCT CAA TCA AGA GGA GGC TAC AGA GAT    3571
Pro Ser Thr Tyr Asp Asp Ile Ser Gln Ser Arg Gly Gly Tyr Arg Asp
                985                 990                 995

GCC TAC AGT TTG CCA CAG AGT GCA ACA ACA GGG ACC GGA TCG CTT TGG    3619
Ala Tyr Ser Leu Pro Gln Ser Ala Thr Thr Gly Thr Gly Ser Leu Trp
            1000                1005                1010

TCC AGA CAG CCC TTT GAG CAG TTT GGT GTA GCG GAG AGG AAT GGT GCT    3667
Ser Arg Gln Pro Phe Glu Gln Phe Gly Val Ala Glu Arg Asn Gly Ala
        1015                1020                1025

GTT GGT GAG GAG CTC AGG AAT AGA TCG AAT CCG ATC AAT ATA GAC AAC    3715
Val Gly Glu Glu Leu Arg Asn Arg Ser Asn Pro Ile Asn Ile Asp Asn
    1030                1035                1040

AAC GCT TCT TCT AAT GTT GAT GCA GAG GCT AAG CTT CTT CAG TCG TTC    3763
Asn Ala Ser Ser Asn Val Asp Ala Glu Ala Lys Leu Leu Gln Ser Phe
1045                1050                1055                1060

AGG CAC TGT ATT CTA AAG CTT ATT AAA CTT GAA GGA TCC GAG TGG TTG    3811
Arg His Cys Ile Leu Lys Leu Ile Lys Leu Glu Gly Ser Glu Trp Leu
                1065                1070                1075

TTT GGA CAA AGC GAT GGA GTT GAT GAA GAA CTG ATT GAC CGG GTA GCT    3859
Phe Gly Gln Ser Asp Gly Val Asp Glu Glu Leu Ile Asp Arg Val Ala
            1080                1085                1090

GCA CGA GAG AAG TTT ATC TAT GAA GCT GAA GCT CGA GAA ATA AAC CAG    3907
Ala Arg Glu Lys Phe Ile Tyr Glu Ala Glu Ala Arg Glu Ile Asn Gln
        1095                1100                1105

GTG GGT CAC ATG GGG GAG CCA CTA ATT TCA TCG GTT CCT AAC TGT GGA    3955
Val Gly His Met Gly Glu Pro Leu Ile Ser Ser Val Pro Asn Cys Gly
    1110                1115                1120
```

```
GAT GGT TGC GTT TGG AGA GCT GAT TTG ATT GTG AGC TTT GGA GTT TGG                4003
Asp Gly Cys Val Trp Arg Ala Asp Leu Ile Val Ser Phe Gly Val Trp
1125                1130                1135                1140

TGC ATT CAC CGT GTC CTT GAC TTG TCT CTC ATG GAG AGT CGG CCT GAG                4051
Cys Ile His Arg Val Leu Asp Leu Ser Leu Met Glu Ser Arg Pro Glu
        1145                1150                1155

CTT TGG GGA AAG TAC ACT TAC GTT CTC AAC CGC CTA CAG GGA GTG ATT                4099
Leu Trp Gly Lys Tyr Thr Tyr Val Leu Asn Arg Leu Gln Gly Val Ile
    1160                1165                1170

GAT CCG GCG TTC TCA AAG CTG CGG ACA CCA ATG ACA CCG TGC TTT TGC                4147
Asp Pro Ala Phe Ser Lys Leu Arg Thr Pro Met Thr Pro Cys Phe Cys
        1175                1180                1185

CTT CAG ATT CCA GCG AGC CAC CAG AGA GCG AGT CCG ACT TCA GCT AAC                4195
Leu Gln Ile Pro Ala Ser His Gln Arg Ala Ser Pro Thr Ser Ala Asn
    1190                1195                1200

GGA ATG TTA CCT CCG GCT GCA AAA CCG GCT AAA GGC AAA TGC ACA ACC                4243
Gly Met Leu Pro Pro Ala Ala Lys Pro Ala Lys Gly Lys Cys Thr Thr
1205                1210                1215                1220

GCA GTC ACA CTT CTT GAT CTA ATC AAA GAC GTT GAA ATG GCA ATC TCT                4291
Ala Val Thr Leu Leu Asp Leu Ile Lys Asp Val Glu Met Ala Ile Ser
        1225                1230                1235

TGT AGA AAA GGC CGA ACC GGT ACA GCT GCA GGT GAT GTG GCT TTC CCA                4339
Cys Arg Lys Gly Arg Thr Gly Thr Ala Ala Gly Asp Val Ala Phe Pro
    1240                1245                1250

AAG GGG AAA GAG AAT TTG GCT TCG GTT TTG AAG CGG TAT AAA CGT CGG                4387
Lys Gly Lys Glu Asn Leu Ala Ser Val Leu Lys Arg Tyr Lys Arg Arg
        1255                1260                1265

TTA TCG AAT AAA CCA GTA GGT ATG AAT CAG GAT GGA CCC GGT TCA AGA                4435
Leu Ser Asn Lys Pro Val Gly Met Asn Gln Asp Gly Pro Gly Ser Arg
    1270                1275                1280

AAA AAC GTG ACT GCG TAC GGA TCA TTG GGT TGA AGAAGAAGAA CATTGTGAGA             4488
Lys Asn Val Thr Ala Tyr Gly Ser Leu Gly *
1285                1290                1295

AATCTCATGA TCAAAGTGAC GTCGAGAGGG AAGCCGAAGA ATCAAAACTC TCGCTTTTGA              4548

TTGCTCCTCT GCTTCGTTAA TTGTGTATTA AGAAAGAAG AAAAAAAATG GATTTTTGTT              4608

GCTTCAGAAT TTTTCGCTCT TTTTTTCTTA ATTTGGTTGT AATGTTATGT TTATATACAT              4668

ATATCATCAT CATAGGACCA TAGCTACAAA CCGAATCCGG TTTGTGTAAT TCTATGCGGA              4728

ATCATAAAGA AATCGTCG                                                            4746
```

(2) INFORMATION FOR SEQ ID NO:3:

(i) SEQUENCE CHARACTERISTICS:
        (A) LENGTH: 1294 amino acids
        (B) TYPE: amino acid
        (D) TOPOLOGY: linear (ii) MOLECULE TYPE: protein (xi) SEQUENCE DESCRIPTION: SEQ ID NO:3:

```
Met Glu Ala Glu Ile Val Asn Val Arg Pro Gln Leu Gly Phe Ile Gln
1               5                   10                  15

Arg Met Val Pro Ala Leu Leu Pro Val Leu Leu Val Ser Val Gly Tyr
                20                  25                  30

Ile Asp Pro Gly Lys Trp Val Ala Asn Ile Glu Gly Gly Ala Arg Phe
            35                  40                  45

Gly Tyr Asp Leu Val Ala Ile Thr Leu Leu Phe Asn Phe Ala Ala Ile
        50                  55                  60

Leu Cys Gln Tyr Val Ala Ala Arg Ile Ser Val Val Thr Gly Lys His
65                  70                  75                  80
```

-continued

```
Leu Ala Gln Ile Cys Asn Glu Glu Tyr Asp Lys Trp Thr Cys Met Phe
                 85                  90                  95
Leu Gly Ile Gln Ala Glu Phe Ser Ala Ile Leu Leu Asp Leu Thr Met
            100                 105                 110
Val Val Gly Val Ala His Ala Leu Asn Leu Leu Phe Gly Val Glu Leu
        115                 120                 125
Ser Thr Gly Val Phe Leu Ala Ala Met Asp Ala Phe Leu Phe Pro Val
    130                 135                 140
Phe Ala Ser Phe Leu Glu Asn Gly Met Ala Asn Thr Val Ser Ile Tyr
145                 150                 155                 160
Ser Ala Gly Leu Val Leu Leu Tyr Val Ser Gly Val Leu Leu Ser
                165                 170                 175
Gln Ser Glu Ile Pro Leu Ser Met Asn Gly Val Leu Thr Arg Leu Asn
            180                 185                 190
Gly Glu Ser Ala Phe Ala Leu Met Gly Leu Leu Gly Ala Ser Ile Val
        195                 200                 205
Pro His Asn Phe Tyr Ile His Ser Tyr Phe Ala Gly Glu Ser Thr Ser
    210                 215                 220
Ser Ser Asp Val Asp Lys Ser Ser Leu Cys Gln Asp His Leu Phe Ala
225                 230                 235                 240
Ile Phe Gly Val Phe Ser Gly Leu Ser Leu Val Asn Tyr Val Leu Met
                245                 250                 255
Asn Ala Ala Ala Asn Val Phe His Ser Thr Gly Leu Val Val Leu Thr
            260                 265                 270
Phe His Asp Ala Leu Ser Leu Met Glu Gln Val Phe Met Ser Pro Leu
        275                 280                 285
Ile Pro Val Val Phe Leu Met Leu Leu Phe Ser Ser Gln Ile Thr
    290                 295                 300
Ala Leu Ala Trp Ala Phe Gly Gly Glu Val Val Leu His Asp Phe Leu
305                 310                 315                 320
Lys Ile Glu Ile Pro Ala Trp Leu His Arg Ala Thr Ile Arg Ile Leu
                325                 330                 335
Ala Val Ala Pro Ala Leu Tyr Cys Val Trp Thr Ser Gly Ala Asp Gly
            340                 345                 350
Ile Tyr Gln Leu Leu Ile Phe Thr Gln Val Leu Val Ala Met Met Leu
        355                 360                 365
Pro Cys Ser Val Ile Pro Leu Phe Arg Ile Ala Ser Ser Arg Gln Ile
    370                 375                 380
Met Gly Val His Lys Ile Pro Gln Val Gly Glu Phe Leu Ala Leu Thr
385                 390                 395                 400
Thr Phe Leu Gly Phe Leu Gly Leu Asn Val Val Phe Val Val Glu Met
                405                 410                 415
Val Phe Gly Ser Ser Asp Trp Ala Gly Gly Leu Arg Trp Asn Thr Val
            420                 425                 430
Met Gly Thr Ser Ile Gln Tyr Thr Thr Leu Leu Val Ser Ser Cys Ala
        435                 440                 445
Ser Leu Cys Leu Ile Leu Trp Leu Ala Ala Thr Pro Leu Lys Ser Ala
    450                 455                 460
Ser Asn Arg Ala Glu Ala Gln Ile Trp Asn Met Asp Ala Gln Asn Ala
465                 470                 475                 480
Leu Ser Tyr Pro Ser Val Gln Glu Glu Ile Glu Arg Thr Glu Thr
                485                 490                 495
Arg Arg Asn Glu Asp Glu Ser Ile Val Arg Leu Glu Ser Arg Val Lys
```

-continued

```
                500             505             510
Asp Gln Leu Asp Thr Thr Ser Val Thr Ser Ser Val Tyr Asp Leu Pro
        515                 520                 525

Glu Asn Ile Leu Met Thr Asp Gln Glu Ile Arg Ser Ser Pro Pro Glu
        530                 535                 540

Glu Arg Glu Leu Asp Val Lys Tyr Ser Thr Ser Gln Val Ser Ser Leu
545                 550                 555                 560

Lys Glu Asp Ser Asp Val Lys Glu Gln Ser Val Leu Gln Ser Thr Val
                565                 570                 575

Val Asn Glu Val Ser Asp Lys Asp Leu Ile Val Glu Thr Lys Met Ala
                580                 585                 590

Lys Ile Glu Pro Met Ser Pro Val Glu Lys Ile Val Ser Met Glu Asn
        595                 600                 605

Asn Ser Lys Phe Ile Glu Lys Asp Val Glu Gly Val Ser Trp Glu Thr
        610                 615                 620

Glu Glu Ala Thr Lys Ala Ala Pro Thr Ser Asn Phe Thr Val Gly Ser
625                 630                 635                 640

Asp Gly Pro Pro Ser Phe Arg Ser Leu Ser Gly Glu Gly Ser Gly Gly
                645                 650                 655

Thr Gly Ser Leu Ser Arg Leu Gln Gly Leu Gly Arg Ala Ala Arg Arg
                660                 665                 670

His Leu Ser Ala Ile Leu Asp Glu Phe Trp Gly His Leu Tyr Asp Phe
        675                 680                 685

His Gly Gln Leu Val Ala Glu Ala Arg Ala Lys Lys Leu Asp Gln Leu
        690                 695                 700

Phe Gly Thr Asp Gln Lys Ser Ala Ser Ser Met Lys Ala Asp Ser Phe
705                 710                 715                 720

Gly Lys Asp Ile Ser Ser Gly Tyr Cys Met Ser Pro Thr Ala Lys Gly
                725                 730                 735

Met Asp Ser Gln Met Thr Ser Ser Leu Tyr Asp Ser Leu Lys Gln Gln
                740                 745                 750

Arg Thr Pro Gly Ser Ile Asp Ser Leu Tyr Gly Leu Gln Arg Gly Ser
        755                 760                 765

Ser Pro Ser Pro Leu Val Asn Arg Met Gln Met Leu Gly Ala Tyr Gly
        770                 775                 780

Asn Thr Thr Asn Asn Asn Ala Tyr Glu Leu Ser Glu Arg Arg Tyr
785                 790                 795                 800

Ser Ser Leu Arg Ala Pro Ser Ser Glu Gly Trp Glu His Gln Gln
                805                 810                 815

Pro Ala Thr Val His Gly Tyr Gln Met Lys Ser Tyr Val Asp Asn Leu
        820                 825                 830

Ala Lys Glu Arg Leu Glu Ala Leu Gln Ser Arg Gly Glu Ile Pro Thr
        835                 840                 845

Ser Arg Ser Met Ala Leu Gly Thr Leu Ser Tyr Thr Gln Gln Leu Ala
850                 855                 860

Leu Ala Leu Lys Gln Lys Ser Gln Asn Gly Leu Thr Pro Gly Pro Ala
865                 870                 875                 880

Pro Gly Phe Glu Asn Phe Ala Gly Ser Arg Ser Ile Ser Arg Gln Ser
                885                 890                 895

Glu Arg Ser Tyr Tyr Gly Val Pro Ser Ser Gly Asn Thr Asp Thr Val
                900                 905                 910

Gly Ala Ala Val Ala Asn Glu Lys Lys Tyr Ser Ser Met Pro Asp Ile
        915                 920                 925
```

```
Ser Gly Leu Ser Met Ser Ala Arg Asn Met His Leu Pro Asn Asn Lys
930                 935                 940

Ser Gly Tyr Trp Asp Pro Ser Ser Gly Gly Gly Tyr Gly Ala Ser
945                 950                 955                 960

Tyr Gly Arg Leu Ser Asn Glu Ser Ser Leu Tyr Ser Asn Leu Gly Ser
                965                 970                 975

Arg Val Gly Val Pro Ser Thr Tyr Asp Asp Ile Ser Gln Ser Arg Gly
            980                 985                 990

Gly Tyr Arg Asp Ala Tyr Ser Leu Pro Gln Ser Ala Thr Thr Gly Thr
        995                 1000                1005

Gly Ser Leu Trp Ser Arg Gln Pro Phe Glu Gln Phe Gly Val Ala Glu
    1010                1015                1020

Arg Asn Gly Ala Val Gly Glu Glu Leu Arg Asn Arg Ser Asn Pro Ile
1025                1030                1035                1040

Asn Ile Asp Asn Asn Ala Ser Ser Asn Val Asp Ala Glu Ala Lys Leu
                1045                1050                1055

Leu Gln Ser Phe Arg His Cys Ile Leu Lys Leu Ile Lys Leu Glu Gly
            1060                1065                1070

Ser Glu Trp Leu Phe Gly Gln Ser Asp Gly Val Asp Glu Glu Leu Ile
        1075                1080                1085

Asp Arg Val Ala Ala Arg Glu Lys Phe Ile Tyr Glu Ala Glu Ala Arg
    1090                1095                1100

Glu Ile Asn Gln Val Gly His Met Gly Glu Pro Leu Ile Ser Ser Val
1105                1110                1115                1120

Pro Asn Cys Gly Asp Gly Cys Val Trp Arg Ala Asp Leu Ile Val Ser
                1125                1130                1135

Phe Gly Val Trp Cys Ile His Arg Val Leu Asp Leu Ser Leu Met Glu
            1140                1145                1150

Ser Arg Pro Glu Leu Trp Gly Lys Tyr Thr Tyr Val Leu Asn Arg Leu
        1155                1160                1165

Gln Gly Val Ile Asp Pro Ala Phe Ser Lys Leu Arg Thr Pro Met Thr
    1170                1175                1180

Pro Cys Phe Cys Leu Gln Ile Pro Ala Ser His Gln Arg Ala Ser Pro
1185                1190                1195                1200

Thr Ser Ala Asn Gly Met Leu Pro Pro Ala Ala Lys Pro Ala Lys Gly
                1205                1210                1215

Lys Cys Thr Thr Ala Val Thr Leu Leu Asp Leu Ile Lys Asp Val Glu
            1220                1225                1230

Met Ala Ile Ser Cys Arg Lys Gly Arg Thr Gly Thr Ala Ala Gly Asp
        1235                1240                1245

Val Ala Phe Pro Lys Gly Lys Glu Asn Leu Ala Ser Val Leu Lys Arg
    1250                1255                1260

Tyr Lys Arg Arg Leu Ser Asn Lys Pro Val Gly Met Asn Gln Asp Gly
1265                1270                1275                1280

Pro Gly Ser Arg Lys Asn Val Thr Ala Tyr Gly Ser Leu Gly
                1285                1290                1295
```

(2) INFORMATION FOR SEQ ID NO: 4:

(i) SEQUENCE CHARACTERISTICS:
        (A) LENGTH: 23 nucleic acids
        (B) TYPE: nucleic acid
        (C) STRANDEDNESS: single
        (D) TOPOLOGY: linear (iv) ANTI-SENSE: no

```
      (xi) SEQUENCE DESCRIPTION: SEQ ID NO: 4:
           GGATCCTCTA GTCAAATTAC CGC                              23

(2) INFORMATION FOR SEQ ID NO: 5:

(i) SEQUENCE CHARACTERISTICS:
         (A) LENGTH: 24 nucleic acids
         (B) TYPE: nucleic acid
         (C) STRANDEDNESS: single
         (D) TOPOLOGY: linear (iv) ANTI-SENSE: no (xi) SEQUENCE DESCRIPTION: SEQ ID NO: 5:
          AGATCTGGTA TATTCCGTCT GCAC                              24

(2) INFORMATION FOR SEQ ID NO: 6:

(i) SEQUENCE CHARACTERISTICS:
         (A) LENGTH: 18 nucleic acids
         (B) TYPE: nucleic acid
         (C) STRANDEDNESS: single
         (D) TOPOLOGY: linear (iv) ANTI-SENSE: no (xi) SEQUENCE DESCRIPTION: SEQ ID NO: 6:
          CCGGATTCGG TTTGTAGC                                     18

(2) INFORMATION FOR SEQ ID NO: 7:

(i) SEQUENCE CHARACTERISTICS:
         (A) LENGTH: 18 nucleic acids
         (B) TYPE: nucleic acid
         (C) STRANDEDNESS: single
         (D) TOPOLOGY: linear (iv) ANTI-SENSE: no (xi) SEQUENCE DESCRIPTION: SEQ ID NO: 7:
          GAAAGCCACA TCACCTGC                                     18

(2) INFORMATION FOR SEQ ID NO: 8:

(i) SEQUENCE CHARACTERISTICS:
         (A) LENGTH: 17 nucleic acids
         (B) TYPE: nucleic acid
         (C) STRANDEDNESS: single
         (D) TOPOLOGY: linear (iv) ANTI-SENSE: no (xi) SEQUENCE DESCRIPTION: SEQ ID NO: 8:
          GACACCGGGA AGTATCG                                      17

(2) INFORMATION FOR SEQ ID NO: 9:

(i) SEQUENCE CHARACTERISTICS:
         (A) LENGTH: 19 nucleic acids
         (B) TYPE: nucleic acid
         (C) STRANDEDNESS: single
         (D) TOPOLOGY: linear (iv) ANTI-SENSE: no (xi) SEQUENCE DESCRIPTION: SEQ ID NO: 9:
          CTGCTTTCAT AGAAGAGGC                                    19

(2) INFORMATION FOR SEQ ID NO: 10:

(i) SEQUENCE CHARACTERISTICS:
         (A) LENGTH: 19 nucleic acids
         (B) TYPE: nucleic acid
         (C) STRANDEDNESS: single
         (D) TOPOLOGY: linear (iv) ANTI-SENSE: no (xi) SEQUENCE DESCRIPTION: SEQ ID NO: 10:
          GTCAGAACAA ACCTGCTCC                                    19
```

(2) INFORMATION FOR SEQ ID NO: 11:

(i) SEQUENCE CHARACTERISTICS:
        (A) LENGTH: 16 nucleic acids
        (B) TYPE: nucleic acid
        (C) STRANDEDNESS: single
        (D) TOPOLOGY: linear (iv) ANTI-SENSE: no (xi) SEQUENCE DESCRIPTION: SEQ ID NO:11:
        GGCCGCCATG GATGCG                                      16

(2) INFORMATION FOR SEQ ID NO: 12:

(i) SEQUENCE CHARACTERISTICS:
        (A) LENGTH: 18 nucleic acids
        (B) TYPE: nucleic acid
        (C) STRANDEDNESS: single
        (D) TOPOLOGY: linear (iv) ANTI-SENSE: no (xi) SEQUENCE DESCRIPTION: SEQ ID NO: 12:
        CTTGAAGGAT CCGAGTGG                                  18

(2) INFORMATION FOR SEQ ID NO: 13:

(i) SEQUENCE CHARACTERISTICS:
        (A) LENGTH: 20 nucleic acids
        (B) TYPE: nucleic acid
        (C) STRANDEDNESS: single
        (D) TOPOLOGY: linear (iv) ANTI-SENSE: no (xi) SEQUENCE DESCRIPTION: SEQ ID NO: 13:
        CTTGCTGTTA TTCTCCATGC                              20

(2) INFORMATION FOR SEQ ID NO: 14:

(i) SEQUENCE CHARACTERISTICS:
        (A) LENGTH: 18 nucleic acids
        (B) TYPE: nucleic acid
        (C) STRANDEDNESS: single
        (D) TOPOLOGY: linear (iv) ANTI-SENSE: no (xi) SEQUENCE DESCRIPTION: SEQ ID NO: 14:
        CTGGCTGGCA GCCACGCC                                  18

(2) INFORMATION FOR SEQ ID NO: 15:

(i) SEQUENCE CHARACTERISTICS:
        (A) LENGTH: 18 nucleic acids
        (B) TYPE: nucleic acid
        (C) STRANDEDNESS: single
        (D) TOPOLOGY: linear (iv) ANTI-SENSE: no (xi) SEQUENCE DESCRIPTION: SEQ ID NO: 15:
        TGGTTGCTGA AGCCAGGG                                  18

(2) INFORMATION FOR SEQ ID NO: 16:

(i) SEQUENCE CHARACTERISTICS:
        (A) LENGTH: 19 nucleic acids
        (B) TYPE: nucleic acid
        (C) STRANDEDNESS: single
        (D) TOPOLOGY: linear (iv) ANTI-SENSE: no (xi) SEQUENCE DESCRIPTION: SEQ ID NO: 16:
        ATGCCCAAGA ACATGCACG                                19

(2) INFORMATION FOR SEQ ID NO: 17:

```
    (i) SEQUENCE CHARACTERISTICS:
        (A) LENGTH: 19 nucleic acids
        (B) TYPE: nucleic acid
        (C) STRANDEDNESS: single
        (D) TOPOLOGY: linear (iv) ANTI-SENSE: no (xi) SEQUENCE DESCRIPTION: SEQ ID NO: 17:
        GTTGTTAGGT CAACTTGCG                                     19

(2) INFORMATION FOR SEQ ID NO: 18:

(i) SEQUENCE CHARACTERISTICS:
        (A) LENGTH: 19 nucleic acids
        (B) TYPE: nucleic acid
        (C) STRANDEDNESS: single
        (D) TOPOLOGY: linear (iv) ANTI-SENSE: no (xi) SEQUENCE DESCRIPTION: SEQ ID NO: 18:
        CTCTGTTAGG GCTTCCTCC                                     19

(2) INFORMATION FOR SEQ ID NO: 19:

(i) SEQUENCE CHARACTERISTICS:
        (A) LENGTH: 18 nucleic acids
        (B) TYPE: nucleic acid
        (C) STRANDEDNESS: single
        (D) TOPOLOGY: linear (iv) ANTI-SENSE: no (xi) SEQUENCE DESCRIPTION: SEQ ID NO: 19:
        GAATCAGATT TCGCGAGG                                      18
```